United States Patent [19]

Iijima et al.

[11] Patent Number: 4,940,665
[45] Date of Patent: Jul. 10, 1990

[54] METHOD FOR GRANULATION OF ENZYME

[75] Inventors: Hitoshi Iijima; Kunio Nishimura, both of Tokyo, Japan

[73] Assignee: Showa Denko K. K., Tokyo, Japan

[21] Appl. No.: 103,550

[22] PCT Filed: Dec. 26, 1986

[86] PCT No.: PCT/JP86/00661

§ 371 Date: Aug. 4, 1987

§ 102(e) Date: Aug. 4, 1987

[87] PCT Pub. No.: WO87/04184

PCT Pub. Date: Jul. 16, 1987

[30] Foreign Application Priority Data

Dec. 27, 1985 [JP] Japan .................. 60-293167

[51] Int. Cl.$^5$ ................................. C12N 9/98
[52] U.S. Cl. ...................... 435/187; 252/174.12; 252/DIG. 12
[58] Field of Search .............. 435/187; 252/174.12, 252/DIG. 12

[56] References Cited

U.S. PATENT DOCUMENTS

| | | | |
|---|---|---|---|
| 3,749,671 | 7/1973 | Gedge, III | 435/187 |
| 3,775,331 | 11/1973 | Borrello | 252/174.12 |
| 4,106,991 | 8/1978 | Markussen et al. | 435/187 |
| 4,572,897 | 2/1986 | Amutz et al. | 435/177 |

FOREIGN PATENT DOCUMENTS

| | | |
|---|---|---|
| 0256127 | 12/1986 | European Pat. Off. . |
| 1935233 | 1/1970 | Fed. Rep. of Germany ... 252/DIG. 12 |
| 1802465 | 5/1970 | Fed. Rep. of Germany . |
| 2030531 | 12/1971 | Fed. Rep. of Germany . |
| 57-165497 | 10/1982 | Japan . |
| 60-168385 | 8/1985 | Japan . |

*Primary Examiner*—Robert A. Wax
*Attorney, Agent, or Firm*—Oblon, Spivak, McClelland, Maier & Neustadt

[57] ABSTRACT

A product obtained by granulating an enzyme powder must avoid emitting dust, possess high strength, exhibit the property of quickly dissolving in water where such ready solution is necessary for the intended application, defy absorption of moisture or deformation for a long time, and preserve without a sacrifice of activity. The method of this invention produces granules of raw enzyme powder possessed of the qualities mentioned above by admixing the enzyme powder with polyethylene glycol or polyoxyethylene-polyoxypropylene block polymer of specific quality as a binder and granulating by agitating the resulting combination at a temperature not lower than the melting point of the binder. This method is suitable for production of enzyme-containing granules for use in detergents, medicines, etc.

5 Claims, No Drawings

METHOD FOR GRANULATION OF ENZYME

TECHNICAL FIELD

This invention relates to a method for the granulation of an industrial grade raw enzyme powder. More particularly, this invention relates to a method for the granulation of a raw enzyme powder, characterized by the fact that spherical particles having diameters in a desired range can be obtained in a high yield with minimum inactivation ratio and without entailing any mechanical trouble and the produced granules possess proper strength, produce almost no dust, excel in storage, and dissolve quickly in water preparatory to actual use.

BACKGROUND ART

The industrial grade enzymes which are used in machines, foods and drinks, textiles, leather, detergents, and various other applications are broadly divided into those obtained by extraction from animals and plants and those obtained as products of fermentation by microorganisms. Generally the enzymes of the former type are economically utilizable only to a limited extent because of limited sources of supply, whereas those of the latter type are extensively used because they have virtually infinite sources of supply and are producible relatively economically.

Generally the enzyme powders, no matter whether they originate in animals and plants or in microorganisms, which hawve been obtained by separation and purification are rarely put to use in their unaltered form. Most of these enzyme powders are granulated by themselves or in combination with an extender, a stabilizer, and other substances and put to use.

The granulated enzymes are generally in demand in particle sizes in the range of about 0.5 to 1.5 mm. Further, as in any other field, the granulated enzymes are required to be uniform in particle size, shape, and constituent makeup, rich in flowability, excellent in mechanical strength, and rigid enough to avoid sustaining cracking and chipping during storage or transportation. Besides these general requirements, the granulated enzymes must fulfill the following requirements.

It has been pointed out that enzymes, particularly proteases (proteolytic enzyme), may cause allergic reactions in some workers and users handling them when the dust of the enzymes comes in contact with the eyes, nose, and skin, for example. Therefore, as much as possible, it is necessary to prevent generation of dust during storage, transport, uses etc.

Mechanical strength and dust emission are not necessarily directly related. For example, some granules are so rigid as to offer fair resistance to disintegration and yet emit a fine dust and other granules are highly disintegrable into minute particles and yet are not reduced into a fine powder. Generally, the so-called elutriation method is used in the determination of the dust-emitting property of granulated enzymes. It is held that granulated enzymes are desirable when the amount of dust emitted thereby as determined by this method is not more than 150 GU/60 g (Ton den Ouden, Tenside Detergents, 14(1977) 4, P 209-210).

In virtually all cases, the granulated enzymes are put to use as dissolved in hot water or cold water. Particularly, in the case of granulated enzymes intended for use in detergents which form a main application for the industrial grade enzymes, from the point of the overall time consumed in laundering, these granulated enzymes must be capable of being quickly dispersed and dissolved to release the enzymes in water in a span of several minutes. Even if a granulated enzyme has high mechanical strength, therefore, it cannot be used as a good product if it possesses poor solubility in water. When an enzyme product having inferior storage stability is kept in storage for a long time, this enzyme product absorbs moisture and consequently swells and deforms, undergose disintegration and coalescence, suffers from loss of flowability and decline of activity, and sustains other forms of degeneration, to the extent of being deprived of its commercial value. The granulated enzymes, therefore, must possess sufficient solubility in water as described above and, on the other hand, absorb moisture only nominally and exhibit satisfactory moisture resistance.

Further, in the granulation of enzyme powder, there is entailed a peculiar important problem. Enzymes are generally liable to be inactivated by heat and water. In numerous cases, their inherent activity is impaired by the heat and water to which the enzymes are exposed during the course of granulation.

Therefore, it is important for granulation method of an enzyme powder to attain the granulation under conditions not capable of inactivating the enzyme, i.e. under conditions using a low temperature and a small amount of water sufficient to preclude the inactivation of enzyme.

Quite naturally, further, the operational conditions involved in the work of granulation such as, for example, length of the time required for the granulation, presence or absence of such mechanical troubles as adhesion of the raw material to the wall of the granulating machine, amount of such adjuvants as a binder to be used, and yield of the granulation (yield of acceptable product), viz. the conditions which may well be termed as economic factors, are equally important elements to be fulfilled.

Thus, the method adopted for the granulation of the enzyme powder can hardly be called satisfactory when it fails to fulfill all at once the numerous requirements mentioned above which, in a sense, turn out to be mutually incompatible requirements.

Various methods have been heretofore proposed as means for the granulation of enzyme powders. Substantially all of these methods, however, contemplate using water or an aqueous solution of a binder substance as the binder for the granules to be produced. Industrial grade enzymes, particularly those various enzymes which are obtained by the culture of microorganisms, generally contain impurities to a certain extent. These impurities manifest strong viscosity in the presence of water. When water is added to the raw material being granulated, therefore, it manifests its function as a binder. Since the binding force (binder property) of these impurities is variable with their composition, it is difficult to attain effective granulation of the enzyme powder under a fixed set of conditions, making it necessary to study the conditions for the granulation for each production lot of the enzyme powder. When the work of granulation is to be carried out in an automated operation, therefore, quality control of the product of this operation is difficult to obtain because the granulated enzyme acquires dispersed properties. A still more important problem arises from the fact that when an enzyme powder is granulated in the presence of water, the produced granules must be dried as by heating for expulsion of the water inevitably incorporated therein. Most emzymes be nature are relatively unstable and are liable to be inactivated in the presence of water. Thus, the presence of water itself can pose a problem. The subsequent exposure of the produced granules to the heat applied thereto for the purpose of drying aggravates the inactivation of an enzyme which inherently is rather unstable with respect to heat. Thus, the enzymatic activity is inevitably lost more or less during the course of the granulation.

Methods have been proposed for granulating enzyme powders in a non-aqueous medium using a waxy substance as a binder without the presence of water. The methods heretofore known to the art have a disadvantage that they require use of a third substance such as a core substance or fibrous substance during the work of granulation and necessitate provision of a complicated apparatus.

The method of Japanese Patent Pulbication SHO 46(1971)-4259, for example, effects the granulation of an enzyme powder by tumbling the raw material while using a viscous waxy substance such as a nonionic surfactant. Since this method requires to use a core substance, it produces granules with an insufficient enzyme content and further suffers from poor productivity.

Japanese Patent Publication SHO 52-47033 discloses a method which effects the granulation of an enzyme by preparing a liquid containing the enzyme and a wax as a binder, dispersing this liquid with centrifugal force, and cooling the dispersed drops of the liquid. This method does not permit a desired increase in the enzyme concentration in the produced granules because it requires use of the wax in an amount of at least 50% by weight based on the total amount of the materials for the granulation. It suffers from poor economy because the apparatus used therefor is voluminous and complicated.

Japanese Patent Publication SHO 58(1983)-26315 discloses a method for the granulation of an enzyme, which requires to use cellulosic fibers in an amount in the range of 2 to 40% by weight and a waxy substance and/or water as a granulating agent in an amount in the range of 50 to 70% by weight. This publicatgion discloses the granulation of alkalase by the use of a water-insoluble ethoxy aliphatic alcohol, as a working example using a waxy substance as a sole granulating agent. For this method, use of cellulosic fibers having an average length in the range of 50 to 160μ and an average width in the range of 20 to 30μ is an essential requirement. The addition of these cellulosic fibers is claimed to preclude deposition of an irremovable layer on the inner wall of the granulating machine and facilitate the control of the granulation. From the practical point of view, however, this method has a disadvantage in that the presence of such fibers requires the waxy substance to be used in a relatively large amount, elongates the time to be spent for the granulation, and aggravates the surface irregularity of produced granules and consequently enhances the generation of dust due to friction of granules.

In the granulation of an enzyme powder, efficiency of the work of granulation, shape and flowability of the produced granules, uniformity in the particle size, shape, and constituent makeup of the produced granules, generation of dust, rigidity, storage stability, solubility of the granules in water preparatory to actual use, and avoidance of the adverse effects exerted on the enzymatic properties by such additives as a binder are equally important considerations besides the problem of loss of activity during the course of granulation. Needless to say, economy constitutes another equally important consideration. The methods heretofore known to the art indeed possess some superior properties and exhibit improved qualities to some extent as described above. None of the conventional methods, however, can fulfill all the aforementioned considerations at once. All of them have some fault or other of their own.

DISCLOSURE OF INVENTION

An object of this invention is to provide a method for the granulation of a raw enzyme powder, characterized by the fact that, in the granulation of the enzyme powder alone or of a powder consisting of the enzyme and such additives as extender, stabilizer, and coloring agent (hereinafter referred to as "raw enzyme powder"), spherical particles having a particle size in a desired range can be produced in a high yield without entailing any mechanical trouble and with the inactivation during the granulation repressed to the fullest possible extent and the produced granules possess sufficient strength, excel in storage stability, produce almost no dust, and dissolve quickly in water preparatory to actual use.

The inventors continued a diligent study in search of a method for the granulation of an enzyme powder, which is capable of attaining the object described above. As a result, they have found that the granulation of an enzyme powder effected by agitating the enzyme powder in a non-aqueous system using a specific wax in an amount falling within a limited range enables uniform and substantially spherical particles to be produced quickly in a high yield without either requiring addition of a fibrous substance or entailing deposition of an irremovable layer on the inner wall of the apparatus during the course of granulation and that the produced granules possess satisfactory strength, excel in storage stability, produce almost no dust, and dissolve quickly in water preparatory to actual use. This invention has been perfected as the result.

To be specific, the present invention is directed to a method for the granulation of a raw enzyme powder by the agitating of the raw enzyme powder admixed with a wax which method comprises adding to the raw enzyme powder in a substantially dry state at least one member in the amount of 10~35 wt % selected as a wax from the group consisting of polyethylene glycol and polyoxyethylene-polyoxypropylene block polymer having melting points in the range of 40° to 100° C. and agitating and granulating the product of the addition at a temperature not lower than the melting point of the added wax.

BEST MODE FOR CARRYING OUT THE INVENTION

Now, the method of the present invention will be described more specifically below.

The enzyme to be granulated by the method of the present invention is not specifically limited. It can be any of the enzymes which are generally used in medicines, foodstuffs, textiles, leather, detergents, and other industrial applications. The method for the granulation contemplated by this invention optimally suits enzymes to be used in detergents. The optimum enzymes for the purpose of this invention are represented by proteases, lipases, amylases, cellulases, and pectinases. One member or a combination of two or more members selected from among these optimum enzymes can be used.

The raw enzyme powder may solely comprise an enzyme powder. Otherwise, it may comprise an additive such as an extender or a filler optionally incorporated as a diluent for the purpose of keeping the specific activity of the produced granules at a prescribed level.

When the raw enzyme powder contains the aforementioned additive, the enzyme content in the raw enzyme powder is required to be at least 5% for the purpose of enabling the enzyme to be homogeneously contained in the produced granules and allowing the produced granules to retain the enzymatic activity sufficiently, though this enzyme content is not invariably fixed because of the influence of the potency of the enzyme itself. Concrete examples of the extender or filler are as follows.

Sulfates: Sodium sulfate, potassium sulfate, calcium sulfate, magnesium sulfate, zinc sulfate, ferrous sulfate, sodium thiosulfate, and aluminum sulfate.

Hydrochlorides and bromides: Sodium chloride, potassium chloride, calcium chloride, magnesium chloride, and potassium bromide.

Carbonates: Sodium carbonte, sodium hydrogen carbonate, potassium carbonate, calcium carbonate, and magnesium carbonate.

Phosphates: Sodium phosphate, sodium hydrogen phosphate, sodium dihydrogen phosphate, potassium phosphate, potassium hydrogen phosphate, potassium dihydrogen phosphate, and sodium pyrophosphate.

Silicates: Sodium silicate, sodium metasilicate, potassium silicate, and calcium silicate.

Boric acid (borates): Borax, potassium borate, and boric acid.

The extender or filler is desired to have a particle size of not more than 100 $\mu$m, preferably not more than 20 $\mu$m. One member or a combination of two or more members selected from the group of extenders and fillers cited above can be used.

Further, any of the coloring agents and stabilizing agents which are known in the fields of granulation and enzyme preparation can be suitably used.

In the method of the present invention, one key to successful granulation of an enzyme powder is the selection of a binder to be used in the raw enzyme powder. For perfect fulfillment of the requirement mentioned above, use of a polyethylene glycol (polyoxyethylene) or a polyoxyethylene-polyoxy propylene block polymer having a melting point in the range of 40° to 100° C. is indispensable. Various substances are conceivable for use in an operation which contemplates using a simply waxy substance as a binder and effecting the granulation in a non-aqueous system. The binders other than those specified above as usable in this invention invariably have merits and demerits of their own and fail to meet the purpose of this invention. For example, such waxy substances as coconut oil monoethanol amide, polyoxyethylene fatty acid ester, polyoxyethylenealkyl ether, polyoxyethylenealkylphenol ether, and glycerin fatty acid ester cannot be used because the granules obtained from the raw enzyme powders using them are invariably deficient in solubility in water. Then, such waxy substances as sorbitan fatty acid ester and sugar wax, mainly because of their high degrees of hygroscopicity, has a disadvantage that the produced granules are deficient in storage stability.

Even among polyethylene glycols (PEG) having a melting point in the vicinity of the aforementioned, those having an average molecular weight falling outside the range of 3,000 to 10,000, for example those with a molecular weight of less than 3,000, do not exhibit good pelletization yields even when granulatable, and the granules are deficient in storage stability. If the molecular weight exceeds 10,000, the molten material prepared for the granulation possesses too high viscosity to be efficiently granulated and, because of the necessity for keeping the temperature at a level high enough to lower the viscosity, the molten material entails inactivation of the enzyme as a drawback during the course of granulation and the granules are produced in a low yield and the produced granules have an inferior shape. To be used in this invention desirably from the practical point of view, therefore, the PEG is required to possess a melting point in the range of 40° to 100° C. and an average molecular weight in the range of 3,000 to 10,000. Preferably, the melting point is in the range of 45° to 70° C. and the average molecular weight in the range of 4,000 to 8,000.

For substantially the same reason as given above, the polyoxyethylene-polyoxypropylene block polymer is desired to have an average molecular weight in the range of 7,000 to 24,000, preferably 8,000 to 15,000. If the melting point is lower, although the molten material can be granulated, the granules are produced in a yield hardly called satisfactory and the produced granules are deficient in storage stability. If the melting point is higher, the molten material is granulated with poor efficiency, entails inactivation of the enzyme as a drawback during the course of granulation, and produces granules in a low yield, and the produced granules have a poor shape.

One member or a combination of two or more members selected from the group consisting of polyethylene glycol and polyoxyethylene-polyoxypropylene block polymers can be effectively used herein. When two or more members are used in combination, the mixture is required to possess a melting point falling in the range mentioned above.

Suitably, the amount of the waxy substance (hereinafter referred to simply as "waxy") to be incorporated in the raw enzyme powder (the total amount of the materials combined for the purpose of granulation) is in the range of 10 to 35% by weight, based on the amount of the raw enzyme powder. If this amount does not reach 10% by weight, the granulation does not produce desired granules but only gives rise to minute particles. If the amount exceeds 35% by weight, the granulation proceeds suddenly in a short span of time and entails a disadvantage that the control of the granulation is not easily obtained and the granules are produced in an extremely low yield.

During the granulation, the wax must be in a molten state. Thus, the granulating machine is heated in advance to a temperature of not lower than the melting point of the wax to be used. While the granulation is in progress, however, the temperature of the granulation machine is desired to be kept down to the lowest possible level because this temperature, if elevated to an unduly high level, can become a cause for inactivation of the enzyme. Generally, the temperature of the granulating machine must be kept at a level higher by a margin in the range of 5° to 20° C. than the melting point of the wax to be used. Desirably this margin is between 7° C. and 12° C., preferably in the neighborhood of 10° C.

The wax which is admixed with the other components for granulation is amply agitated therein for thorough mixing with the other components. During this agitating, desired granulation is attained at the prescribed temperature.

The wax can be added in a molten state or in a solid state to the other components for the granulation. In either case, the outcome of the granulation is the same. The procedure which comprises preparatorily heating the wax and subsequently adding the wax now in a molten state by spraying onto the other components for granulation shortens the time required for the granulation and consequently improves the productivity.

For the granulation contemplated by this invention, it is an essential requirement that the granulation should be effected by agitating the molten material. None of the conventional methods available for granulation, can attain the desired granulation fulfilling the requirements set by this invention.

To be specific, the granulation of this invention is carried out by placing the raw enzyme powder (enzyme powder alone or combined with the other additives) and the wax powder in the granulating machine kept in advance at a temperature high enough to melt the wax used as the binder and agitating the contents of the granulating machine.

As regards the water content of the raw enzyme powder for granulation, if the water content is unduly high, the excess of water can be a cause for inactivation of the enzyme during the course of granulation. Practically, it must be kept not higher than 10% by weight, preferably not higher than 8% by weight.

After the granulation is completed, the granules consequently produced are cooled, recovered from the granulating machine, when necessary, withe aid of a small amount of a release agent, and then overcoated to give rise to a finished product.

The overcoating of the produced granules is carried out by keeping the granules tumbled in the agitating-granulating machine or some other rotary machine, adding a binder, namely a wax, in a molten state to the granules in motion and, at the same time or subsequently, adding thereto other surface-covering substances such as, for example, a coloring agent, stabilizing agent, excipient, deodorant, and antistatic agent. The aforementioned binder may be added in a comminuted solid state and then heated and melted while being rolled in conjunction with the granules in the rotary machine.

The was to be used for the overcoating must be selected strictly for the same reason as already given with respect to the binder which is used for the granulation.

As the binder to be used for overcoating the granules of this invention, one polyethylene glycol or a mixture of two or more such polyethylene glycols and/or a polyoxyethylene-polyoxypropylene block polymer or a mixture of two or more such block polymers, each possessing a melting point of not lower than 35° C. and not higher than the softening point of the binder which is used for the granulation, is used. One member or a combination of two or more members selected from the binders enumerated above can be used.

With any of the binders other than those cited above, the coating desired to be attained by this invention cannot be obtained for the same reason as already described with respect to the binder for the granulation.

If a binder is similar in kind to the binder used for the aforementioned overcoating but has a melting point lower than 35° C., then the coated granules produced by the procedure of this invention is deficient in storage stability. If a binder has a melting point exceeding the softening point of the coated granules exude to the surface and the finished product finally obtained does not withstand actual use.

Although the amount of the binder to be used for the aforementioned overcoating is suitably variable with the condition of surface finish of the granules, the composition of the surface-covering agent, and the amount of this surface-covering agent to be used, it generally falls in the range of 6 to 8% by weight, based on the weight of the produced granules.

A white coloring agent to be used herein is desired to be a sparingly hygroscopic inorganic substance such as titanium oxide, talc, and/or zeolite comminuted to a particle size in the range of 1 to 100 $\mu$m. Although the amount of the coloring agent to be used in suitably variable, it generally falls in the range of 13 to 17% by weight, based on the amount of the produced granules.

Other covering substances such as excipient, deodorant, and antistatic agent may be added when needed.

Where the property of dust emission must be repressed further or the storage stability must be improved further, the coated granules may be re-overcoated with the aforementioned binder.

Now, the method of the present invention will be more specifically described below with reference to typical working examples. Needless to say, these examples are meant purely for illustration and not for limiting the present invention in any sense.

The tests for the determination of enzymatic activity and for the evaluation of the results of granulation were carried out in accordance with the methods indicated below.

(1) Determination of activity of protease: The method disclosed in Japanese Patent Publication SHO 60(1985)-55118.

(2) Determination of activity of amylase: The "method for testing industrial grade amylase for liquefying power" defined by JIS K 7001-1972.

(3) Determination of activity of cellulase: The method described in "Handbook on Use of Enzymes", page 298, compiled under supervision of Michio Kozaki (published by Chijin Shokan).

(4) Determination of activity of lipase: The method described on page 230 of the aforementioned Handbook.

(5) Detemination of activity of pectinase: The method described on page 338 of the aforementioned Handbook.

(6) Ratio of inactivation during granulation: The radio expressed bu the formula, $$\frac{A - B}{A} \times 100,$$

using the value (A) of the activity of a given raw enzyme powder fed and the value (B) of the activity of the enzyme in the recovered granules, both determined by the relevant method described above.

(7) Bulk density: Method in compliance with JIS K 3362.

(8) Whiteness: The method proposed by Hunter for the determination of whiteness.

(9) Solubility in water: The ratio expressed by the formula, $$\frac{\text{Value of activity of enzyme in solution}}{\text{Value of activity of enzyme of sample}} \times 100 \, (\%),$$

using the value of activity of a given enzyme powder and the value of activity of enzyme in a solution obtained by agitating 1 g of the sample for 3 minutes in 100 g of water at 10° C., both determined by the relevant method described above.

(10) Storage stability: The stability expressed by the residual ratio of activity in percentage points (%), found by the ratio of the values of activity of a given enzyme granule before and after two weeks standing under the conditions of 40° C. and 80% humidity, both determined by the relevant method described above. The sample after the standing was further examined visually as to change of shape and occurrence of coalescence of granules.

(11) Property of dust emission: The method (elutriation) described in Ton den Ouden: Tenside Detergents, 14 (1977) 4, P 209–210.

EXAMPLE 1

In a jacketed agitating and granulating machine, 340 g of protease powder (API-21, 80 nkatal/mg), 1,230 g of anhydrous sodium sulfate, 80 g of titanium oxide, and 350 g of polyethylene glycol (a product marketed under Code "PEG-5000", having an average molecular weight of 5,000 and a melting point of about 85° C.) were mixed by agitating for 2 minutes, with the main shaft of the machine operated at a rate of 250 rpm and the chopper thereof at a rate of 3,000 rpm. Under the same agitating conditions as described above, the resulting mixture was granulated as continuously heated by passing hot water at 70° C. through the jacket.

The granulation was completed in a total span of 31 minutes. Then, 15 g of finely comminuted silica was added to the granules and agitated therewith and the resultant mixture was discharged, cooled by fluidizying and then recovered. Thus, 1,995 g of mixture was recovered, indicating a recovery ratio of 99.0%. Substantially no deposition of any material on the inner wall of the granulating machine was recognized.

The particle size distribution of the granules consisted of 3.9% of 14-mesh on, 95% of 14–42 mesh, and 1.1% of 42-mesh pass. The yield (yield of granulation) of the acceptable granules (14–42 mesh) was as high as 94.1%. By observation under an optical microscope, these granules were found mostly to be spheres having a smooth surface. The results of the test of these granules for static and impact strengths indicate that they possessed ample strength. The ratio of inactivation during granulation was found to be 1.3%, indicating that substantially no inactivation occurred during the operation of granulation.

The acceptable granules obtained be sifting were overcoated as follows. The granules, 1.890 g, were placed again in the aforementioned agitating and granulating machine and heated to 45° C. Then, to the heated granules, polyethylene glycol (a product marketed under Code "PEG 1540", having an average molecular weight of 1,500 and a melting point of about 43° C.) was added as a melt in an amount of (132 g) corresponding to 7% by weight, based on the amount of the granules. The contents of the machine were mixed by agitating for two minutes with the main shaft of the machine operted at a rate of 150 rpm (the chopper not used). Thereafter, the granules and titanium oxide added thereto in an amount (283 g) corresponding to 15% by weight, based on the amount of the granules, were mixed under the aforementioned agitating conditions for five minutes. After this mixing, the contents of the machine were discharged.

The overcoated granules were recovered in an amount of 2305 g (100%), indicating that the ratio of inactivation was 0%. They had a bulk density of 1.09 and a Hunter's whiteness of 80%, a value representing ample whiteness (the whiteness held to be necessary from the practical point of view is not less than 75%). By observation under an optical microscope, they were found to be spheres having a smooth surface. The results of test for static and impact strength indicate that the overcoated granules possessed ample strength. In the test for solubility in water, they showed a solubility ratio of 99%, a value indicating highly satisfactory solubility in water. In the test for stability over two weeks' storage, the residual ratio of activity was found to be 61%, a value representing ample stability. The property of dust emission determined by the elutriation method was 60 GU/60 g, a value amply satisfying the standard (150 GU/60 g) required to be met for the sake of safety of handling.

As described above, the product obtained in the present example met all the requirements expected to be possessed by a granulated enzyme, indicating that this product had highly satisfactory qualities.

EXAMPLE 2

The aforementioned agitating and granulating machine was filled with 340 g of protease powder (API-21, 80 nkat/mg), 25 g of raw amylase powder (a product of Yamato Kasei, 220000 $L_J$/g, marketed under the trademark of "Crystase M20"), 1155 g of anhydrous sodium sulfate, 80 g of titanium oxide, and 400 g of the same polyethylene glycol as used in Example 1, and granulation was performed by the same procedure as in Example 1. The whole procedure was completed in a span of 30 minutes.

The amount of produced granules recovered was 2003 g, representing a recovery ratio of 99.4%. Substantially no deposition of any material on the inner wall of the machine was observed.

The particle size distribution consisted of 3.1% of 14-mesh on, 94.2% of 14–42 mesh, and 2.7% of 42-mesh pass. The yield of granulation was 93.6%. By observation under an optical microscope, the granules were found substantially to be spheres having a smooth surface. They showed ample static and impact strength.

The ratios of inactivation of protease and amylase during granulation were 1.3% and 1.6% respectively, indicating that substantially no discernible inactivation was caused by the operation of granulation.

The acceptable granules, 1,880 g, obtained by sifting were overcoated by following the procedure of Example 1, except that the amount of polyethylene glycol to be used was changed to 113 g.

The product of this overcoating had a bulk density of 1.08 and a Hunter's whiteness of 82%. By observation under an optical microscope, the granules were found to be spheres having a smooth surface. They showed a solubility ratio of 99%, indicating that they possessed highly satisfactory solubility in water. In the test for storage stability, the residual ratio of activity was 65%, a value representing ample storage stability. The property of dust emission determined by the elutriation method was 40 GU/60 g. Thus, the product obtained in this example possessed highly satisfactory qualities for a granulated enzyme.

EXAMPLE 3

Granules were produced by following the procedure of Example 1, except that polyethylene glycolpolypropylene glycol block polymer (a product of Dai-ichi Kogyo Seiyaku Co., Ltd., having a melting point of about 60° C. and marketed under trademark designation of "Epan 785") was used in place of polyethylene glycol. The whole procedure was completed in a span of 32 minutes.

The amount of granules recovered was 1,996 g, representing a recovery ratio of 99.1%. Substantially no deposition of any material on the inner wall of the machine was observed. The particle size distribution consisted of 4.5% of 14-mesh on, 93.7% of 14–42 mesh, and 1.8% of 42-mesh pass. The yield of granulation was 92.8%. By observation under an optical microscope, the granules were found substantially to be spheres having a smooth surface. They possessed ample static and impact strength. The ratio of inactivation during granulation was 1.8%, a value indicating that substantially no discernible inactivation was caused by the operation of granulation.

The acceptable granules, 1,860 g, obtained by sifting was overcoated by following the procedure of Example 1.

The overcoated product had a bulk density of 1.09 and a Hunter's whiteness of 80%. By observation under an optical microscope, these granules were found to be spheres having a smooth surface. The solubility ratio was 98%, a value representing highly satisfactory solubility in water. In the test for storage stability, the ratio of residual activity was 61%, indicating that the granules possessed ample storage stability. The property of dust emission determined by the elutriation method was 55 GU/60 g.

EXAMPLE 4

Granules were produced by following the procedure of Example 2, except that polyethylene glycolpolypropylene glycol block polymer (Epan 785) was used in place of polyethylene glycol. The whole procedure was completed in a span 30 minutes.

The amount of granules recovered was 2,001 g, representing a recovery ratio of 99.3%. Substantially no deposition of any material on the inner wall of the machine was recognized. The particle size distribution consisted of 4.2% of 14-mesh on, 93.8% of 14–42 mesh, and 2.0% of 42-mesh pass. The yield of granulation was 93.1%. By observation under an optical microscope, the produced granules were found substantially to be spheres having a smooth surface. They showed ample static and impact strength. The ratios of inactivation of protease and amylase during granulation were 1.9% and 2.0% respectively, indicating that substantially no inactivation was caused by the operation of granulation.

The acceptable granules, 1,870 g, obtained by sifting was overcoated by following the procedure of Example 1, except that 150 g of polyethylene glycol (a product having a molecular weight of 1,900–2,000) marketed under Code of PEG-2000 was used in place of the polyethylene glycol used in Example 1.

The overcoated product had a bulk density of 1.08 and a Hunter's whiteness of 81%. By observation under an optical microscope, these granules were found to be spheres having a smooth surface. The solubility ratio was 98%, a value representing highly satisfactory solubility in water. In the test for storage stability, the granules showed a ratio of residual activity of 62%, a value representing ample storage stability. The property of dust emission determined by the elutriation method was 63 GU/60 g.

EXAMPLES 5, 6 7, and 8

Granules were produced by following the procedure of Example 1, except that other species of enzymes were used in place of the protease used in Example 1, and the kind and amount of a binder and the kind and amount of a coating material were varied from those of Example 1. The conditions of granulation and the results are collectively shown in Table 1.

It is noted from this table that the times required for the granulation were invariably short and the granules were obtained in high recovery ratios. The acceptable granules obtained in high recovery ratios represent highly satisfactory yields of granulation. The ratios of inactivation during granulation were very low.

By observation under an optical microscope, the granules obtained in the different runs were invariably found substantially to be spheres having a smooth surface. They also showed ample static and impact strength.

The finished products obtained by overcoating the acceptable granules with the aforementioned coating material were tested for various properties. The results are shown collectively in Table 2.

The values of Hunter's whiteness the coated products showed were invariably equal to or in excess of 80% and the solubility ratios they showed were invariably equal to or in excess of 97%, a value representing highly satisfactory solubility in water.

In the test for storage stability, while the product of Example 7 showed a relatively low value of 58%, the products of the other examples showed high values exceeding 60%, a level representing satisfactory stability.

TABLE 1

| | EXAMPLE 5 | EXAMPLE 6 | EXAMPLE 7 | EXAMPLE 8 |
|---|---|---|---|---|
| Binder | PEG-4000 (molecular weight 3000–3700) | PEG-6000 (molecular weight 7800–9000) | PEG-4000 (molecular weight 3000–3700) | PEG-6000 (molecular weight 7800–9000) |
| Weight (%) | 12.0 | 12.5 | 30.0 | 15.0 |
| Melting point (°C.) | 43.5–57.5 | 60–63 | 43.5–57.5 | 60–63 |
| Coating material | PEG-1540 (moleuclar weight 1300–1600) | PEG-2000 (molecular weight 1900–2100) | PEG-1500 (molecular weight 500–600) | PEG-1540 (molecular weight 1300–1600) |
| Weight (%) | 8.0 | 7.0 | 7.0 | 6.0 |
| Melting point (°C.) | 43–46 | 50–53 | 38–41 | 43–46 |
| Time required for completion of granulation (min.) | 30 | 32 | 31 | 33 |
| Amount recovered (g) | 1994 | 1997 | 2001 | 1994 |
| Recovery ratio (%) | 99.0 | 99.1 | 99.3 | 99.0 |
| Deposition of material on inner wall | none | none | none | none |

TABLE 1-continued

|  | EXAMPLE 5 | EXAMPLE 6 | EXAMPLE 7 | EXAMPLE 8 |
| --- | --- | --- | --- | --- |
| Particle size distribution (%) | | | | |
| Above 14 mesh | 3.7 | 4.1 | 3.6 | 4.2 |
| Between 14 and 42 mesh | 94.0 | 94.1 | 93.6 | 94.2 |
| Below 42 mesh | 2.3 | 1.8 | 2.8 | 1.6 |
| Yield of granulation | 93.0 | 93.3 | 92.9 | 93.2 |
| Ratio of inactivation during granulation | 1.8 | 2.0 | 1.5 | 1.7 |

TABLE 2

|  | EXAMPLE 5 | EXAMPLE 6 | EXAMPLE 7 | EXAMPLE 8 |
| --- | --- | --- | --- | --- |
| Bulk density | 1.09 | 1.10 | 1.07 | 1.08 |
| Hunter's whiteness | 80.0 | 81.0 | 81.0 | 80.0 |
| Solubility in water | 98.0 | 98.0 | 97.0 | 99.0 |
| Storage stability | 61 | 60 | 58 | 61 |
| Property of dust emission (GU/60 g) | 55 | 60 | 80 | 45 |

COMPARATIVE EXPERIMENT 1

In the aforementioned agitating and granulating machine, 360 g of protease powder (API-21, 80 nkatal/mg), 910 g of anhydrous sodium sulfate, 60 g of titanium oxide, 200 g of cellulose (a product of Sanyo-Kokusaku Pulp Co., Ltd. marketed under the trademark "KC Flock W-100"), and 500 g of talc were mixed by agitating for three minutes. While the contents of the machine were kept agitated under the same conditions as those of Example 1, except that the temperature was changed to 35° C., 300 g of water as a binder was added by a two-flow spray to the agitated contents over a period of 10 minutes. To the contents held under observation for growth of particles, water was gradually added as a binder. The whole procedure of granulation was completed in a span of 39 minutes. The total amount of water thus added was 360 g. The produced granules were discharged, dried by being fluidized at an inlet gas temperature of 80° C. for 15 minutes, and then recovered. The amount of granules thus recovered was 2,195 g (recovery ratio of 93%). There was observed heavy deposition of material on the inner wall of the machine, as compared with the operation of Example 1.

The particle size distribution of the produced granules consisted of 15.0% of 14-mesh on, 80.1% of 14–42 mesh, and 4.9% of 42-mesh pass and the yield of granulation was 74.5%. These results are inferior to those of the granules of Example 1. By observation under an optical microscope, the produced granules were relatively uneven in shape, comprising spheres and ellipsoids both having an irregular surface. The ratio of inactivation during granulation was 3.7%, a value larger than that of the granules of Example 1.

The acceptable granules, 1,000 g, obtained by sifting were overcoated by following the procedure of Example 1.

The overcoated product had a bulk density of 1.04 and a Hunter's whiteness of 79%. By observation under an optical microscope, the granules are found to be spheres having a smooth surface. The solubility ratio was 90%, a value smaller than that of the granules of Example 1. In the test for storage stability, the coated product showed a ratio of residual activity of 60%. The property of dust emission determined by the elutriation method was 140 GU/60 g, a value larger than that of the product of Example 1.

COMPARATIVE EXPERIMENT 2

Granules were produced by following the procedure of Comparative Experiment 1, except that the addition of cellulose was omitted and 1,110 g of anhydrous sodium sulfate and 160 g of water as a binder were added instead.

The amount of granules recovered was 1,865 g, representing a recovery ratio of 79%. There was observed heavy deposition of material on the inner wall of the granulating machine. The particle size distribution of the produced granules consisted of 66.6% of 14-mesh on, 30.7% of 14–42 mesh, and 2.7% of 42-mesh pass. Granules rejectable because of excessive particle size accounted for the major part of the produced granules. The yield of acceptable granules was 24.3%. By observation under an optical microscope, these produced granules were found to be uneven in shape, comprising spheres and ellipsoids having an irregular surface.

These results indicate that the present procedure using water as a binder and not using cellulose entailed many disadvantages such as heavy deposition of material on the inner wall of the machine, unduly large diameters of produced granules, and an extremely low ratio of granulation.

COMPARATIVE EXPERIMENT 3

Granules were produced by following the procedure of Example 1, except that 370 g of protease powder (API-21, 80 nkatal/mg), 860 g of anhydrous sodium sulfate, 60 g of titanium oxide, 200 g of cellulose (a product of Sanyo-Kokusaku Pulp Co., Ltd. marketed under the trademark "KC Flock W-100"), and 510 g of polyethylene glycol (PEG-5000) were used instead. The whole procedure of granulation required 65 minutes. The produced granules were discharged and recovered in the same way as in Example 1. The amount of granules recovered was 1,830 g, representing a recovery ratio of 91%. The deposition of material to the inner wall of the machine was slightly heavier than in the operation of Example 1.

The particle size distribution of the produced granules consisted of 6.9% of 14-mesh on, 83.6% of 14–42 mesh, and 9.5% of 42-mesh pass. The yield of granulation was 75.9%, a value appreciably inferior to the value of the granules of Example 1. By observation under an optical microscope, the granules were found to be relatively uneven in shape, comprising spheres and ellipsoids having an irregular surface. The results of the test for static and impact strength indicate that the granules possessed ample strength. The ratio of inactivation during granulation was 1.5%, a value representing substantial absence of inactivation by the operation of granulation.

The acceptable granules, 1,450 g, obtained by sifting were coated by following the procedure of Example 1 to give rise to a finished product.

The overcoated product possessed a bulk density of 1.05 and a Hunter's whiteness of 81%. By observation under an optical microscope, the granules were found to comprise spheres and ellipsoids having a smooth surface. The solubility ratio was 98%, a value representing highly satisfactory solubility in water. In the test for storage stability, the ratio of residual activity was 60%, indicating ample stability. The property of dust emission was 136 GU/60 g, a value inferior to that of the granules of Example 1.

COMPARATIVE EXPERIMENT 4

Granules were produced by following the procedure of Example 1, except that 360 g of protease powder, 1,160 g of anhydrous sodium sulfate, 80 g of titanium oxide, and 400 g of coconut oil monoethanol amide were charged into and granulated by the aforementioned agitating and granulating machine and the temperature of the hot water was changed to 77° C. The whole procedure of granulation required 53 minutes.

The amount of granules recovered was 1,955 g, representing a recovery ratio of 97.0%. The deposition of material on the inner wall of the machine was slight. The particle size distribution consisted of 16.2% of 14-mesh on, 82.8% of 14–42 mesh, and 1.0% of 42-mesh pass. The yield of granulation was 80.3%.

The yield of granulation was low and not satisfactory as compared with that of the granules of Example 1.

By observation under an optical microscope, the produced granules were found to be spheres having a smooth surface. They showed ample static strength. The ratio of inactivation during granulation was 1.9%, indicating substantial absence of inactivation by the operation of granulation.

The acceptable granules, 1,000 g, obtained by sifting were overcoated by following the procedure of Example 1.

The overcoated product possessed a bulk density of 1.09. By observation under an optical microscope, the granules were found substantially to be spheres having a smooth surface. In the test for storage stability, the ratio of residual activity was found to be 61%. The property of dust emission determined by the elutriation method was 90 GU/60 g, representing a low level of dust emission from the practical point of view. The solubility ratio was only 45%.

The product obtained in this comparative experiment had a lower yield of granulation and a lower solubility ratio than the product obtained in Example 1. Particularly in terms of solubility in water, the product was unfit for actual use.

COMPARATIVE EXPERIMENT 5

Granules were produced by following the procedure of Example 1, except that polyethylene glycolpolypropylene glycol block polymer (a product of Dai-ichi Kogyo Seiyaku Co., Ltd. having a melting point of 35° C. and marketed under trademark designation of "Epan 465") was used in place of polyethylene glycol.

The amount of granules recovered was 1,993 g, representing a recovery ratio of 98.9%. Substantially no deposition of any material on the inner wall of the granulating machine was recognized. The particle size distribution consisted of 5.1% of 14-mesh on, 84.0% of 14–42 mesh, and 10.9% of 42-mesh pass. The yield of the acceptable granules was 83.1%, a value about 10% lower than that of the granules in Example 1.

By observation under an optical microscope, the produced granules were found substantially to be spheres having a smooth surface. They showed ample static and impact strength. The ratio of inactivation during granulation was 1.8%, indicating substantial absence of inactivation by the operation of granulation.

The acceptable granules, 1,660 g, obtained by sifting were overcoated by following the procedure of Example 1 with PEG-1000 (molecular weight 1,000 and melting point 40° C.) used as a coating wax, at a temperature of 40° C.

The overcoated product showed signs of exudation of a coloring component in the raw enzyme powder to the surface granules. The coated granules failed to assume a white color (Hunter's whiteness of 69%) sufficient for the intended use of the product. In the test for storage stability, the produced granules underwent partial coalescence. The ratio of residual activity was 27.0%, a value representing appreciably heavy inactivation.

COMPARATIVE EXPERIMENT 6

Granules were produced by following the procedure of Example 1, except that polyethylene glycol (a product having a molecular weight of 2,000 and a melting point of about 49° C. and marketed under Code "PEG-2000") was used in place of the polyethylene glycol (Code "PEG-5000").

The amount of granules recovered was 1,992 g, representing a recovery ratio of 98.9%. Substantially no deposition of any material on the inner wall of the granulating machine was observed. The particle size distribution of the produced granules consisted of 6.0% of 14-mesh on, 82.3% of 14–42 mesh, and 11.7% of 42-mesh pass, indicating that the yield of granulation was 81.4%. This value is about 10% lower than that of the granules obtained in Example 1. By observation under an optical microscope, the produced granules were found substantially to be spheres having a smooth surface. They showed sufficient static and impact strength.

The acceptable granules, 1,640 g, obtained by sifting were overcoated by following the procedure of Comparative Experiment 1.

The overcoated product showed signs of exudation of a coloring component in the raw enzyme powder to the surface of granules. The coated granules did not assume a white color (Hunter's whiteness 69%) sufficient for the intended use of the product.

In the test for storage stability, the produced granules showed a ratio of residual activity of 58%.

COMPARATIVE EXPERIMENT 7

Granules were produced by following the procedure of Example 1, except that fructose (having a melting point of 105° C.) was used in place of polyethylene glycol and the temperature of heating was changed to 120° C.

The amount of granules recovered was 1,995 g, representing a recovery ratio of 99.0%. Substantially no deposition of any material on the inner wall of the granulating machine was observed. The particle size distribution of the produced granules consisted of 20.2% of 14-mesh on, 71.1% of 14-42 mesh, and 8.7% of 42-mesh pass. The granules underwent coalescence to an extent of increasing the ratio of rejectable granules of 14-mesh on. The yield of the produced granules was notably lowered to 70.4%. The ratio of inactivation during granulation was 14.7%, indicating the occurrence of heavy inactivation by the operation of granulation.

COMPARATIVE EXPERIMENT 8

Granules were produced by following the procedure of Example 1, except that PEG-12000 (having a molecular weight of 12,000 and a melting point of about 63.0° C.) was used in place of PEG-5000 and the temperature of heating was changed to 90° C.

The amount of granules recovered was 1,994 g, representing a recovery ratio of 99.0%. Substantially no deposition of any material on the inner wall of the granulating machine was observed. The particle size distribution of the produced granules consisted of 21.1% of 14-mesh on, 73.5% of 14-42 mesh, and 5.4% of 42-mesh pass. Because of the occurrence of coalescence of granules, the ratio of rejectable granules of 14-mesh on was increased. The yield of granulation was 72.8%, representing a significant decline. The ratio of inactivation during granulation was 15.1%, indicating heavy inactivation by the operation of granulation.

COMPARATIVE EXPERIMENT 9

Granules were produced by following the procedure of Example 1, except that 1,420 g of anhydrous sodium sulfate and 160 g of PEG-5000 were used instead and the time for granulation was increased to 120 minutes. No acceptable granules could be produced.

As to the particle size distribution of the produced granules, all the granules passed a 42-mesh sieve.

The same operation of granulation was repeated using PEG-species having different molecular weights of 3,000 to 10,000. No granules were obtained in any of the test runs.

COMPARATIVE EXPERIMENT 10

Granules were produced by following the procedure of Example 1, except that 820 g of anhydrous sodium sulfate and 760 g of PEG-5000 were used instead.

Two minutes after the temperature of the raw enzyme powder in the granulating machine had reached 59° C., the molten material suddenly formed granules and this formation of granules could not easily be controlled.

The ratio of recovery was 90% and deposition of material on the inner wall of the machine was observed. The particle size distribution consisted of 70.7% of 14-mesh on, 29.1% of 14-42 mesh, and 0.2% of 42-mesh pass. Thus, the particle sizes were notably concentrated on the 14-mesh on.

The operation mentioned above was repeated using PEG-species having different molecular weights of 3,000 to 10,000 and fixing the amounts of addition at 38%. The granulation which proceeded could not be controlled in any of the test runs.

INDUSTRIAL APPLICABILITY

By the method for granulation of enzyme powder according to this invention, the following effects can be obtained.

(1) Since it is a specific wax that manifests the binding force required, the conditions of granulation are stable and need not be varied by the attributes of the raw enzyme powder to be used. Thus, the product of granulation acquires properties with little variance.

(2) Since no water is added, the inactivation of enzyme is very slight and the enzyme activity and the yield of granulation are high.

(3) Since the granulation can be carried out under substantially the same set of conditions even when the attributes of the raw material powder are varied, the productivity of the granulation by the method of the present invention is notably high.

(4) In the granulation in an aqueous system, when the binder property originating in the raw enzyme powder is manifested to an excessive extent, the deposition of material to the inner wall of the granulating machine occurs heavily and the number of times of cleaning of the granulating machine is consequently high. By the method of the present invention, the deposition of material can be substantially eliminated without requiring addition of fibers.

(5) The amount of a wax to be used is small, the time to be spent for granulation is shortened to half, and the yield of granulation is high as compared with the conventional granulation using fibers. The granules produced are uniform in shape and have a smooth surface. Thus, they enjoy a good appearance and yield to the phenomenon of dust emission due to friction of granules to an extremely limited extent.

(6) The produced granules have low hygroscopicity, exhibit satisfactory storage stability, and excel in solubility in water. The granulated product, therefore, manifests its effect as soon as it is put to use.

(7) When two or more species of enzymes, such as protease and amylase, are used in a mixed state, they do not interact within the produced granules while the granules are kept in storage, unlike the granules produced in an aqueous system. Thus, the granules have no possibility of being inactivated during the storage.

The method of this invention for the granulation of an enzyme powder will find extensive utility in medicines, foods and drinks, textiles, leather, detergents and numerous other applications.

We claim:

1. A method for the granulation of a raw enzyme powder, comprising the steps of:
adding to a raw enzyme powder in a substantially dry state at least one wax selected from the group consisting of (1) polyethylene glycol having a melting point in the range of 40°-100° C. and an average molecular weight in the range of 3,000-10,000 and (2) polyoxyethylene-polyoxypropylene block copolymers having a melting point within the range of 40°-100° C. and an average molecular weight in the range of 7,000-24,000, in an amount in the range of 10-35% by weight based on the amount of said raw enzyme powder to obtain a mixture;
agitating said mixture at a temperature 5°-20° C. higher than the melting point of said at least one wax to obtain a granular material;
cooling said granulated material; and
adding to said cooled granular material at least one molten binder selected from the group consisting of (i) polyethylene glycol having a melting point of not less than 35° C. and not higher than the softening point of said wax and (ii) polyoxyethylene-polyoxypropylene block copolymer having a melting point of not less than 35° C. and not higher than said softening point of said wax, while tumbling said cooled granular material, thereby overcoating the granules of said material with said at least one binder.

2. The method of claim 1, wherein the amount of said at least one binder added to the cooled granules is 6–8% by weight based on the amount of said cooled granules.

3. The method of claim 1, wherein said polyethylene glycol wax has a melting point in the range of 45°–70° C. and an average molecular weight ranging from 4,000–8,000.

4. The method of claim 1, wherein said polyoxyethylene-polyoxypropylene block copolymer has an average molecular weight ranging from 8,000–15,000.

5. The method of claim 1, wherein the temperature at which the mixture of raw enzyme powder and wax is agitated ranges from 7°–12° C.

* * * * *